(12) United States Patent
Richmond et al.

(10) Patent No.: US 10,548,548 B2
(45) Date of Patent: Feb. 4, 2020

(54) SYSTEM AND METHOD FOR VISUALIZING A REGISTRATION

(71) Applicant: MIM Software Inc., Cleveland, OH (US)

(72) Inventors: James Howard Richmond, Solon, OH (US); Jerimy Brockway, Aurora, OH (US); Paul Daniel Jacobs, Beachwood, OH (US); Jonathan William Piper, Orange, OH (US)

(73) Assignee: MIM Software, Inc., Cleveland, OH (US)

( * ) Notice: Subject to any disclaimer, the term of this patent is extended or adjusted under 35 U.S.C. 154(b) by 12 days.

(21) Appl. No.: 15/292,276

(22) Filed: Oct. 13, 2016

(65) Prior Publication Data
US 2018/0108133 A1   Apr. 19, 2018

(51) Int. Cl.
*A61B 6/00*   (2006.01)

(52) U.S. Cl.
CPC .................................. *A61B 6/466* (2013.01)

(58) Field of Classification Search
None
See application file for complete search history.

(56) References Cited

U.S. PATENT DOCUMENTS

2012/0197656 A1\* 8/2012 Lang ...................... G06Q 10/10
  705/2

OTHER PUBLICATIONS

Visutsak, Porawat. "Grid transformation for image registration and morphing." The 6th International Conference on Science, Technology and Innovation for Sustainable Well-Being (STISWB VI). 2014. (Year: 2014).\*

\* cited by examiner

*Primary Examiner* — Nirav G Patel
(74) *Attorney, Agent, or Firm* — Tucker Ellis LLP (57) ABSTRACT

Systems and methods to visualize a registration utilize a visual aid, displayed in connection with an image, which is deformed according to the registration. A selected amount of transformation based on the registration can be applied to the image and the visual aid to generate a visualization of movement of respective portions of the image from an original state to a final state.

40 Claims, 11 Drawing Sheets

Secondary Image 710 (overlaying primary image)

Transform

Fig. 7

Transformed Secondary Image 720

SYSTEM AND METHOD FOR VISUALIZING A REGISTRATION

BACKGROUND OF THE INVENTION

1. Field of the Invention

This application relates generally to deformable image registration and, more specifically, to systems and methods for visualizing a transformation resulting from a deformable registration of images.

2. Description of Related Art

Medical imaging systems, such as computed tomography (CT), magnetic resonance (MR), ultrasound (US), positron emission tomography (PET), or the like, produce a two-dimensional image of a patient. These systems can further capture a series of two-dimensional images of the patient which form slices of a three-dimensional volume of the patient. While these medical images provide useful information alone, additional information is gained through comparisons between medical images. For instance, comparisons between medical images facilitate condition monitoring, treatment planning, and/or diagnosis. Such comparisons can be between slices of a single capture volume of a patient, between slices of different volumes of a patient (e.g., captured at different times), or between images captured via different modalities (e.g. ultrasound and MR).

To enable comparisons, the images can be registered through utilization of a registration algorithm such as a deformable registration algorithm having a large number of degrees of freedom. Such registration can result in a high degree of warping to the images in order to be brought into alignment. Moreover, various locations undergo differing amounts of transformation and/or directions of movement. While flexibility in the transform enables dramatically varying images to be registered, interpreting or evaluating the transformation can be difficult.

BRIEF SUMMARY OF THE INVENTION

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

In various, non-limiting embodiments, a visualization technique provides a graphical representation of transforms generated from a registration of a movable image to a reference image. A visual aid, such as a grid, can be superimposed on the movable image and transformed or deformed concurrently with the movable image as specified by the registration to the reference image. The visual aid enables observation of a deformation field associated with the registration, which may not be readily apparent in the underlying image data. Moreover, variable levels of transformation, according to the registration, can be applied to the movable image and/or the visual aid. Thus, transformation of the movable image and/or the visual aid can be animated or displayed in a controllable, step-wise manner based on user input. Transitioning the movable image in this fashion enables movement of respective portions of the movable image according to the registration to be perceived by the user.

These and other embodiments are described in more detail below.

BRIEF DESCRIPTION OF THE DRAWING

Various non-limiting embodiments are further described with reference the accompanying drawings in which.

DETAILED DESCRIPTION OF THE INVENTION

General Overview

As discussed in the background, deformable registration algorithms can produce non-uniform transformations of an image. That is, different portions of the image can undergo transformations differing in both direction and/or magnitude. Thus, understanding the registration is difficult.

In various, non-limiting embodiments, a system and associated methods are provided for visualizing a registration. A registered image is transformed from a first, non-altered state to a second, altered state. To enhance interpretation and evaluation of the transformation, a visualization is generated that indicates changes between the first state and the second state for the registered image. According to one example, the visualization can demonstrate movement of a portion of the image between the first state and the second state. For instance, the image can be visually morphed (e.g. animated) from the first state to the second state. The visual morph can be user-controlled (i.e. via user input) so as to step forwards or backwards through a plurality of intermediate states between the first state and the second state. Accordingly, through the animation, a user can track movement of portions of the image to understand how the registration transforms the image.

According to another example, the visualization can include a graphical element displayed in association with the image. The graphical element can undergo a similar transformation as the image. However, the graphical element is designed such that respective transformations of respective portions are readily perceived. For instance, the graphical element can be a grid overlaying the image. A point on the grid is transformed, according to the registration, identically to a point on the image on which the point on the grid overlays. As the grid is a graphical element having a regular shape and regular spacing, deformation of the grid according to the registration, provides a useful analog to interpret the deformation of the image.

In one embodiment, a method for visualizing a registration is described herein. The method includes receiving a first image and receiving a registration of the first image to a second image. The method can further include outputting the first image to a display device and visually morphing the first image, as displayed on the display device, from a first state to a second state based at least in part on the registration.

According to an example, the method can also include receiving a user input via an input device. The user input effects a change in an amount of transformation, based on the registration, to apply to the first image. The amount of transformation selectable inclusively ranges between a first level corresponding to no transformation applied to a second level corresponding to a complete transformation applied. In an aspect, the user input specifies an increase in the amount of transformation such that morphing the first image includes increasing the amount of transformation applied for the first state to generate the second state. In another aspect, the user input specifies a decrease in the amount of transformation such that morphing the movable image includes decreasing the amount of transformation applied for the first state to generate the second state.

According to another example, morphing includes visually displaying, on the display device, a transition of the first image from the first state to the second state. The transition can be an animation. The first state corresponds to an original state of the first image and the second state corresponds to a fully registered state of the first image according to the registration.

In yet another example, the method can include generating an overlay displayed in association with the first image on the display device and morphing the overlay in concert with the first image. The overlay can be a grid graphically overlaying the first image. Further to this example, morphing the overlay in concert with the first image includes maintaining a relationship between the overlay and the movable image and spatially transforming a location of the overlay and a location of the first image, associated by the relationship, identically in accordance with the registration. The method can further include configuring the overlay such that a feature of the overlay is mapped to a point of interest of the first image.

According to another embodiment, a system is described. The system includes a transformation engine configured to apply a spatial transformation to a first image to transition the first image from a first state to a second state. A registration of the first image to a second image specifies the spatial transformation. The system further includes a display engine configured to output a visualization of the spatial transformation applied to the first image to display device. The visualization demonstrates movement of the first image from the first state to the second state based on the spatial transformation applied. The system further includes a computer-readable storage medium having stored thereon computer-executable instructions for the transformation engine and the display engine such that the computer-executable instructions, when executed by a processor, configure the processor to implement the transformation engine and the display engine.

In an example, the system also includes a registration engine configured to generate the registration between the first image and the second image. The registration engine utilizes a deformable registration technique to generate the registration. The visualization includes a visual aid overlaying the first image. The transformation engine is further configured to apply the spatial transformation to the visual aid. The visual aid can include a feature mapped to a point of interest of the first image. In an example, the visual aid is a grid.

According to further examples, the transformation engine is further configured to determine an amount of transformation to apply to the first image to generate the second state of the first image. The amount of transformation indicates a relative change from a first level of transformation applied for the first state to a second level of transformation corresponding to the second state. The relative change represents one of an increase or a decrease in a level of transformation between the first state and the second state. The first state and the second state represent respective states of spatial transformation on a spectrum from an original, untransformed state to a fully transformed state in accordance with the registration.

In addition, the system can include a user interface configured to generate a graphical user interface displayable by the display engine and to obtain a user input, via an input device, with respect to the graphical user interface. The transformation engine can determine at least one of the first state or the second state based at least in part on the user input. For example, responsive to the user input, the transformation engine applies the spatial transformation to the first image and the display engine interactively displays the movement of the first image from the first state to the second state. The transformation engine is further configured to identify a level of transformation to apply and to scale a full transformation specified by the registration according to the level of transformation.

In yet another embodiment, a computer-readable storage medium is described. The computer-readable storage medium stores computer-executable instructions that, when executed by a processor, configure the processor to: apply a spatial transformation to a first image to transform the first image from a first state to a second state; generate a visualization of movement of one of more portions of the first image due to application of the spatial transformation; and output the visualization to a display device to demonstrate the movement of the one or more portions for a user. In an example, the computer-executable instructions stored on the computer-readable storage medium further configure the processor to output the visualization as an animation. The computer-executable instructions stored on the computer-readable storage medium can further configure the processor to generate the visualization as a grid overlaying the first image. The computer-executable instructions can configure the processor to configure the grid such that a feature of the grid is mapped to a point of interest of the first image. The computer-executable instructions can further configure the processor to apply the spatial transformation to the grid such that a grid location is transformation identically to an image location on which the grid location overlays. The computer-readable storage medium further includes computer-executable instructions that configure the processor to receive a user input, and to interactively control the output of the visualization responsive to the user input.

An overview of some embodiments of visualizing a registration has been presented above. As a roadmap for what follows next, registration visualization is described in more detail. Afterwards, an exemplary computing device and computing environment, in which such embodiments and/or feature described above can be implemented, are described. The above noted features and embodiments will be described with reference to the drawings, wherein like reference numerals are used to refer to like elements throughout.

Image Registration Visualization

As mentioned above, in various embodiments, a visualization is generated to facilitate evaluation and interpretation of an image registration. As some registrations utilize deformable registration techniques having many degrees of freedom, various portions of an image experience different amounts of transformation. Given this non-uniformity, it becomes difficult to perceive the transformation. The visualization generated according to one or more embodiments described herein provides an additional frame of reference and/or a visual guide to illustrate the transformation. With the visualization, respective movement of portions of the image can be readily observed.

Figure 1:
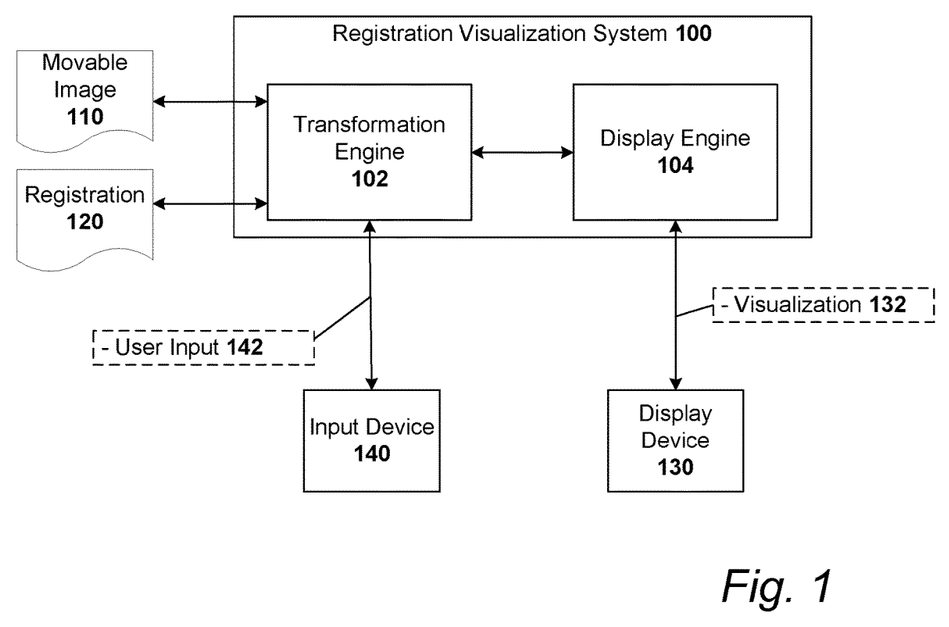
FIG. 1 is a block diagram of an exemplary, non-limiting embodiment for a registration visualization system according to one or more aspects.

FIG. 1 shows a block diagram illustrating an exemplary, non-limiting embodiment for a registration visualization system 100. As shown, registration visualization system 100 can include a transformation engine 102 and a display engine 104. According to an example, registration visualization system 100 can be implemented as a computing device having a processor and various computer-readable storage media (e.g., volatile and non-volatile). The computer-readable storage media can store computer-executable instructions implementing at least a portion of the functional modules, such as transformation engine 102 and display engine 104, depicted in FIG. 1. When the computer-executable instructions are executed by the processor, the registration visualization system 100 is thus configured to perform the operations described herein.

As a computing device, the registration visualization system 100 can further include various hardware devices (not shown) to implement portions of transformation engine 12 and display engine 104. For instance, registration visualization system 100 can include a graphics device having a graphics processing unit (GPU), dedicated memory, and/or hardware interfaces to couple the graphics device to a display such as display device 130. Moreover, registration visualization system 100 can include physical hardware ports and/or wireless interfaces (e.g., Bluetooth, wireless USB, etc.) to couple registration visualization system 100 to various input devices such as input device 140.

In an aspect, the transformation engine 102 receives as input a movable image 110 and a registration 120. Registration 120 can specify a transform, or parameters of a transform, capable of aligning movable image 110 to a reference image (not shown). That is, registration 120 enables movable image 110 to be transformed such that image features (e.g. anatomical features in the case of medical images) are aligned with corresponding image features of the reference image. Registration 120 can provide a rigid (linear) registration or a non-rigid (elastic or deformable) registration.

In an example, movable image 110 can be a medical image generated by a medical imaging apparatus such as, but not limited to, magnetic resonance imaging (MRI), computed tomography (CT), ultrasound, positron emission tomography (PET), optical coherence tomography (OCT), or the like. Various imaging modalities can generate two-dimensional (2D) images or slices. A plurality of 2D images can collectively form a three-dimensional (3D) image or volume. Thus, movable image 110 can be a 2D image or a 3D volume.

Transformation engine 102 can apply a transformation specified by registration 120 to movable image 110 to generate a transformed or registered image. As shown in FIG. 1, the transformed image can be provided to display engine 104, which generates display data output to display device 130 for viewing by a user. According to an aspect, display data can include a visualization 132 that provides graphical and/or visual assistance to promote evaluation or interpretation of the transformation applied to movable image 110.

In one example, the transformation engine 102 is configured to apply varying degrees of transformation to movable image 110. For instance, transformation engine 102 can output movable image 110 having no transformation applied (i.e. 0% transformed), output the image fully transformed (i.e. 100% transformed), and/or output the image having any intermediate level of transformation applied. Accordingly, transformation engine 102 can generate a plurality of transformed images corresponding to varying levels of transformation applied to movable image 110. The plurality of transformed images can be collected by display engine 104 to generate an animation as one example of visualization 132. The animation enables the user to identify and follow movement of portions of movable image 110 as a result of the transformation specified by registration 120.

An amount or degree of transformation applied to movable image 110 can be controlled via a user providing user input 142 via input device 140. For instance, user input 142 can specify the amount of transformation to be applied to movable image 110 such that display engine 104 outputs the movable image 110, thus transformed, to display device 130. In another example, the user input 142 can indicate a step increase or a step decrease to the amount of transformation applied to enable the user to step through the transformation incrementally. That is, the user, via user input 142, can control the animation described above in a step-wise manner forwards and/or backwards to better evaluate movement of image features according to registration 120.

In addition to image data variably transformed based on registration 120, visualization 132 output to display device 130 can include an additional visual aid to facilitate interpretation of registration 120. In one aspect, the visual aid can be a grid which can overlay movable image 110. The grid can be a graphical mesh or tessellation that creates a series of contiguous cells. In one example, the cells can be homogenous. However, it is to be appreciated that the grid can comprise a plurality of cells respectively varying in shape and size. For instance, the grid can be irregular, but the irregularities are configured to generally correspond to anatomical features of movable image 110 so as to optimize the visual aid to particulars of the movable image 110. For example, the grid is configured such that features (e.g. gridlines or intersections of gridlines) correspond to points of interest of the movable image 110. With this correspondence, transformation of the points of interest is better understood. Moreover, the grid can have nested grids such that each cell formed from a primary grid includes a secondary grid forming a plurality of cells. The grid can be configurable (e.g., via user input 142) so as to alter grid spacing, cell size, cell shape, etc. according to preference.

The visual aid included in visualization 132 can be transformed according to registration 120 by transformation engine 102. For example, the visual aid overlays movable image 110. Locations of the visual aid corresponding (e.g. overlying) to respective locations of the movable image 110 are transformed identically by the transformation engine 102. Thus, the transformed images provided to display engine 104 for output include a transformed movable image 110 and a similarly transformed visual aid.

Figure 2:
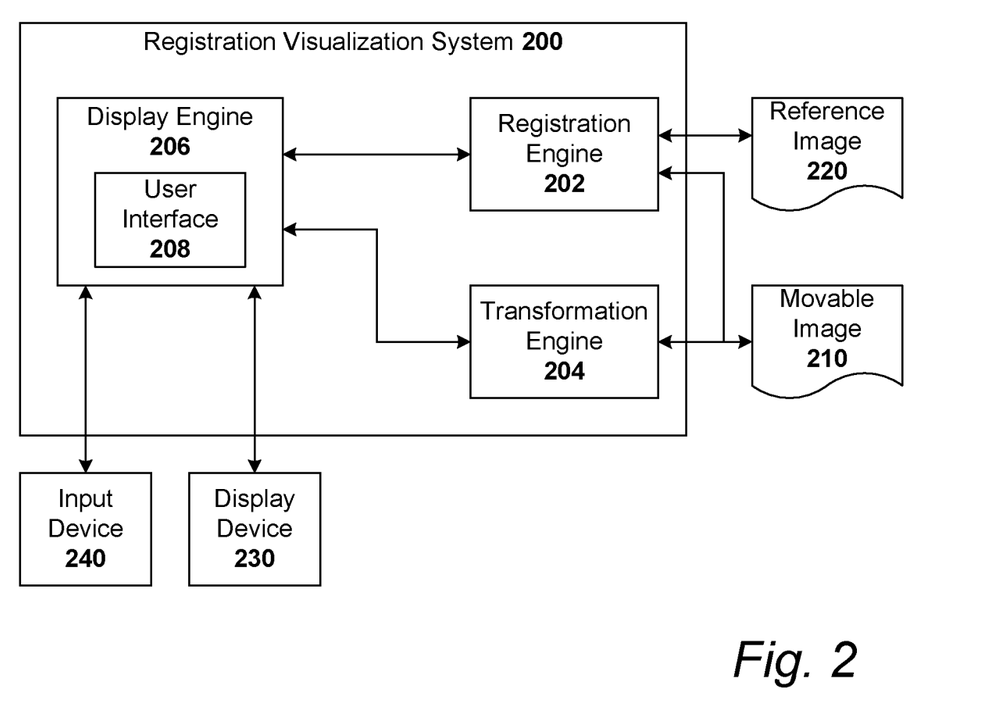
FIG. 2 is a schematic block diagram of an exemplary, non-limiting embodiment for a registration visualization system according to various aspects.

Turning to FIG. 2, illustrated is a schematic block diagram of an exemplary, non-limiting embodiment for a registration visualization system 200 according to various aspects. As shown in FIG. 2, registration visualization system 200 includes a transformation engine 204 and display engine 206 substantially similar to transformation engine 102 and display engine 104 described above. However, as shown in FIG. 2, display engine 206 further generates and maintains a user interface 208 which is output a user via a display device 230 and which accepts or prompts user input from the user via input device 240. For example, user input can configure a visualization, select images from an image store (e.g. PACS server or the like), trigger computation of a registration, and/or control output of the visualization.

Registration visualization system 200 further includes a registration 202 configured to generate a registration between a movable image 210 and a reference image 220. Registration engine 202 can provide a rigid or non-rigid transformation to movable image 210 with respect to reference image 220. The registration can be provided to transformation engine 204 to transform movable image 210 accordingly. As described above, transformation engine 204 can selectively apply a variable amount of transformation inclusively between no transformation and a full transformation. The transformed movable image 210 can be provided to display engine 206 for output to display device 230 as a part of, or in connection with, user interface 208. In addition, transformation engine 204 can similarly transform a visual aid (e.g. a grid or other overlay) in accordance with the registration. The visual aid is output to display device 230 along with the transformed movable image 210 to illustrate movement of portions of the underlying movable image 210 as a result of the registration.

Figure 3:
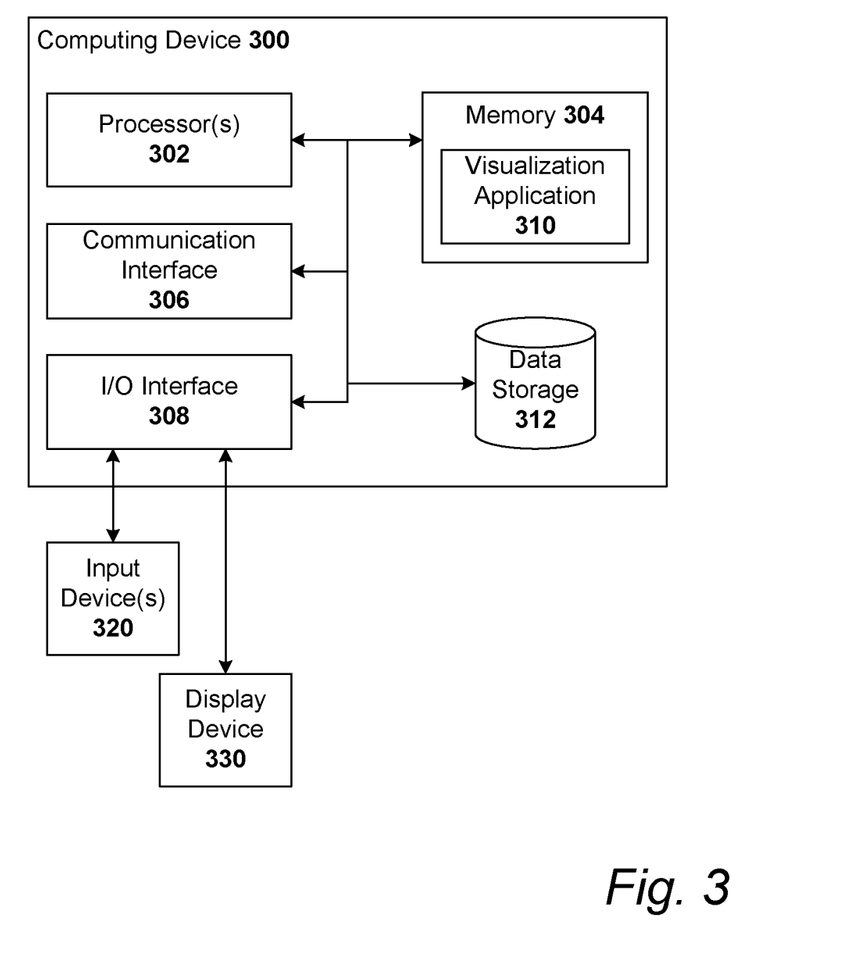
FIG. 3 is a schematic block diagram of an exemplary, non-limiting embodiment for a computing device.

FIG. 3 illustrates a schematic block diagram of an exemplary, non-limiting embodiment for a computing device 300. According to an example, computing device 300 can implement registration visualization system 100, 200 described above. As shown in FIG. 3, computing device 300 includes one or more processor(s) 302 configured to executed computer-executable instructions such as instructions composing a visualization application 310. Such computer-executable instructions can be stored on one or more computer-readable media including non-transitory, computer-readable storage media such as memory 304 and/or data storage 312. For instance, data storage 312 can persistently store visualization application 310 and memory 308 can store visualization application 310 (or a portion thereof) during execution by processor 302.

Computing device 300 includes a communication interface 306 to couple computing device 300 to various remote systems (e.g. an image data store, an imaging apparatus, etc.). Communication interface 306 can be a wired or wireless interface including, but not limited, a WiFi interface, an Ethernet interface, a fiber optic interface, a cellular radio interface, a satellite interface, etc. An I/O interface 308 is also provided to couple computing device 300 to various input and output devices such as display device 330 and input device(s) 320. By way of example, I/O interface 308 can include wired or wireless interfaces such as, but not limited to, a USB interface, a serial interface, a WiFi interface, a short-range RF interface (Bluetooth), an infrared interface, a near-field communication (NFC) interface, etc.

Figure 4:
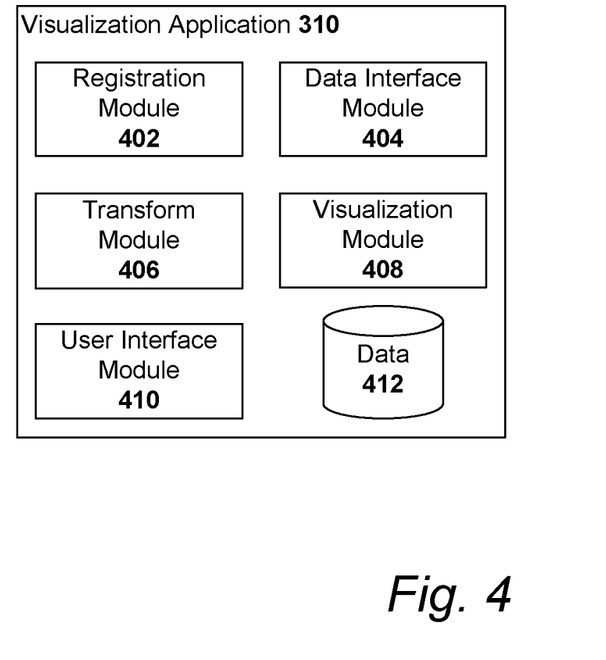
FIG. 4 is a block diagram of an exemplary, non-limiting visualization application according to one or more aspects.

Turning now to FIG. 4, a block diagram of an exemplary, non-limiting visualization application 310 is depicted. As shown in FIG. 4, visualization application 310 can include various functional modules implemented by computer-executable instructions. The modules can include a registration module 402, a data interface module 404, a transform module 406, a visualization module 408, and a user interface module 410. Visualization application 310 can further include various data 412 such as user preferences, configurable settings, working data, temporary data, cached data, processed images, or the like.

Registration module 402 generates a registration between at least two images—a reference image and a movable image. Registration module 402 can utilize a rigid registration which includes linear transformations such as rotation, scaling, translation, and other affine transformations. Alternatively, registration module 402 can employ a non-rigid registration technique such as deformation field having many degrees of freedom. In an example, the images processed by the registration module 402 can be obtained from an image storage device or server via data interface module 404.

Based on a registration, which is either generated by the registration module 402 or retrieve from separate storage by data interface module 404, the transform module 406 can apply the transform specified to a selected image. As described above, the transform can be applied at varying levels ranging from zero transformation to fully transformed, inclusively. The visualization module 408 can generate a visual aid, such as a grid, that can overlay the image. The transform module 406 is configured to apply the transformation specified by the registration to the visual aid. For instance, based on the overlay, a visual relationship is created between points on the visual aid and points of the image. The transform module 406 applies the registration transform identically to related points of the visual aid and image. The visual aid and image, thus transformed, can be provided to the user interface module 410 to be displayed as part of, or in concert with, a user interface output to a display device. The user interface can further include user operable controls to effect changes in the image displayed, the visual aid, the amount of transformation applied, or the like.

Figure 5:
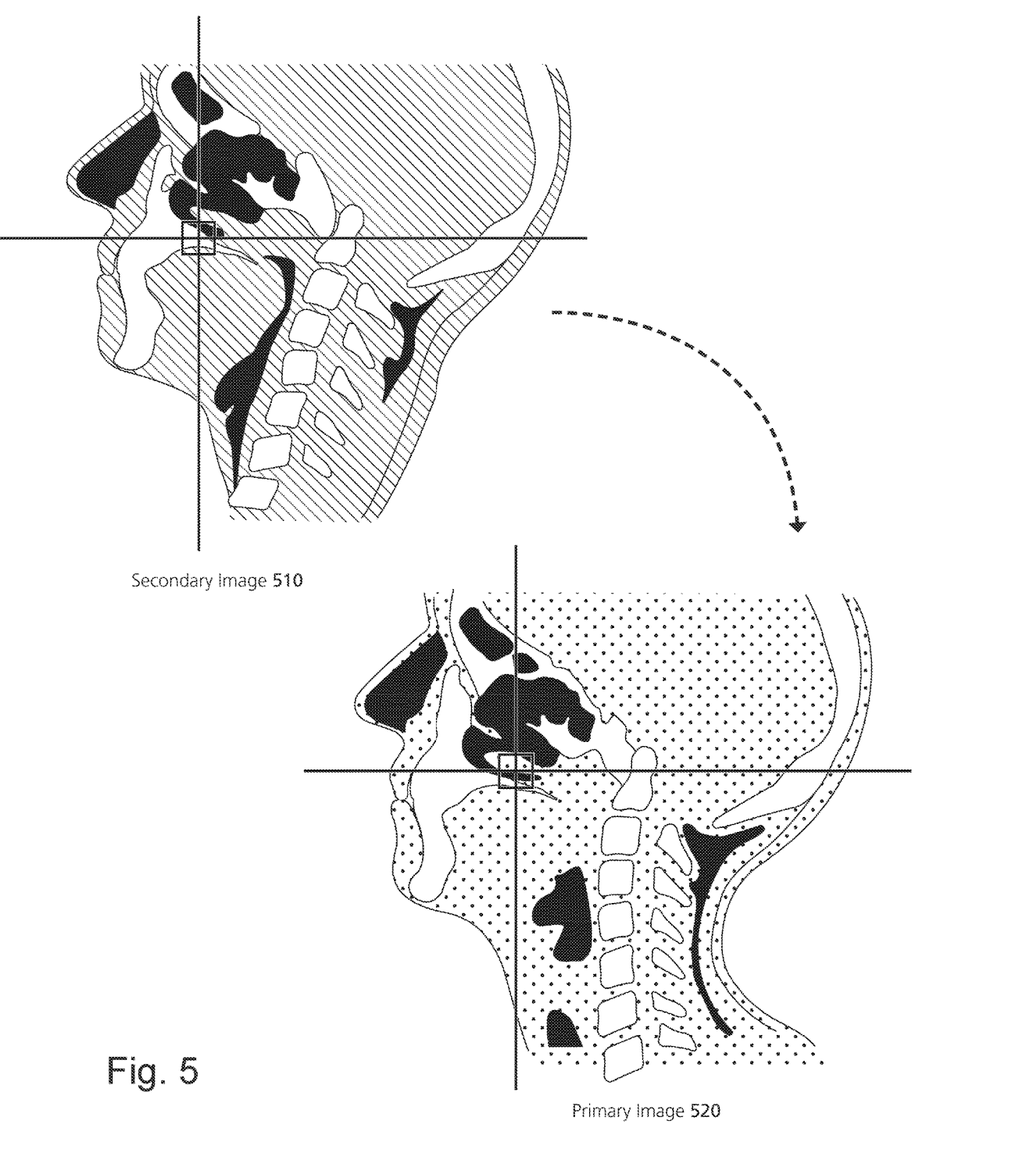
FIG. 5 illustrates an exemplary pair of images selected for registration.
Figure 6:
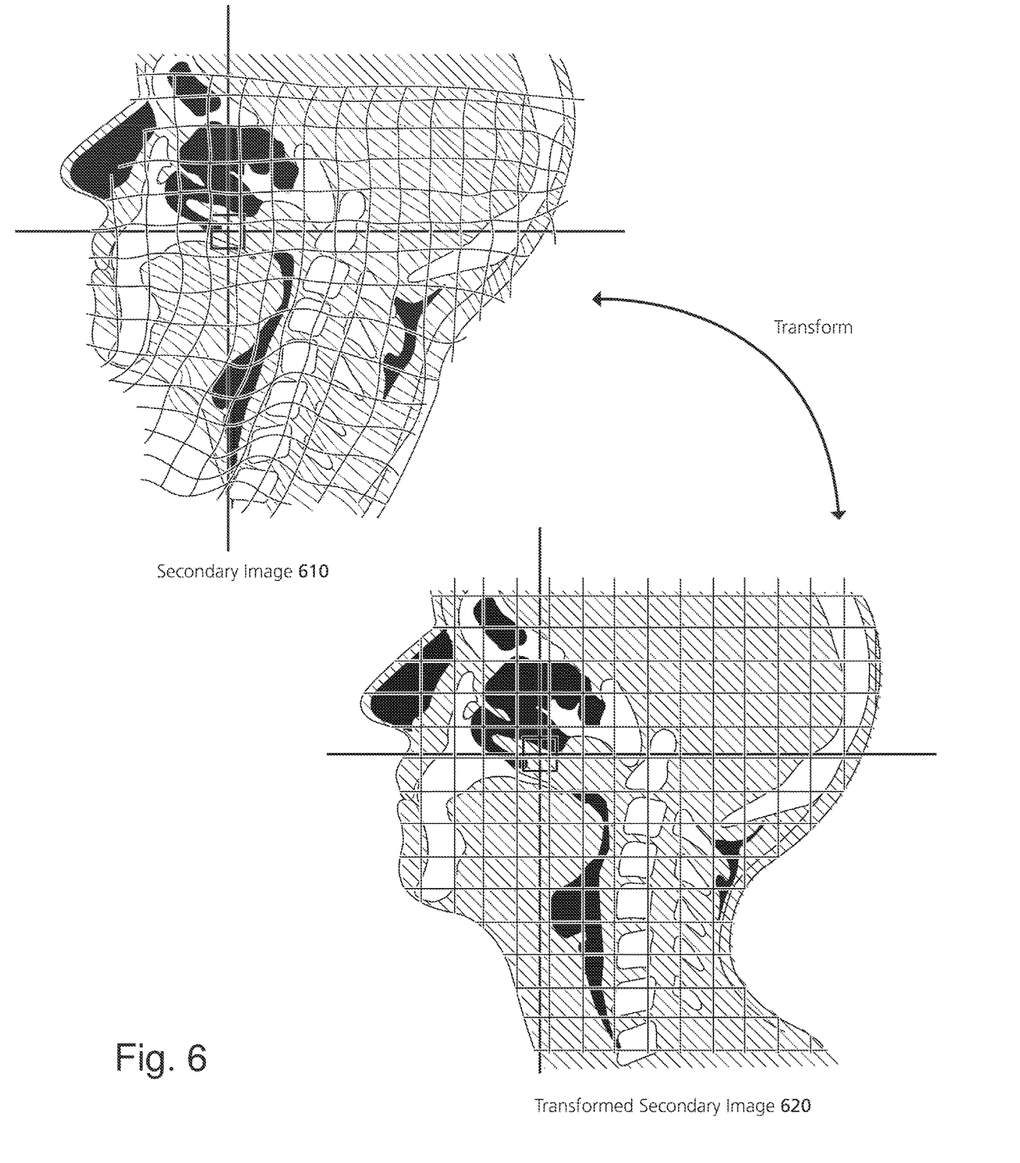
FIG. 6 illustrates a transformation of an image according to an aspect.

Turning now to FIG. 5, an exemplary pair of images selected for registration is depicted. FIG. 5 includes a secondary image 510 (depicted with parallel hatching in FIG. 5) to be registered to primary image 520 (depicted with stippling). According to this example, secondary image 510 is transformed (e.g. according to a deformable registration) to align with primary image 520. In FIG. 6, the secondary image 510 is illustrated having a visual aid (e.g., grid) overlaid thereon. After application of a registration computed between secondary image 510 and primary image 520, secondary image 510 becomes transformed secondary image 610. As shown in FIG. 6, the visual aid is similarly transformed along with secondary image 510. In the example of FIG. 6, the visual aid is shown as a regular, straight grid when fully transformed according to the registration and as a warped grid in an original, untransformed state. However, it is to be appreciated that the inverse is possible where the regular, straight grid corresponds to the original image and the warped grid results after application of the transform.

Figure 7:
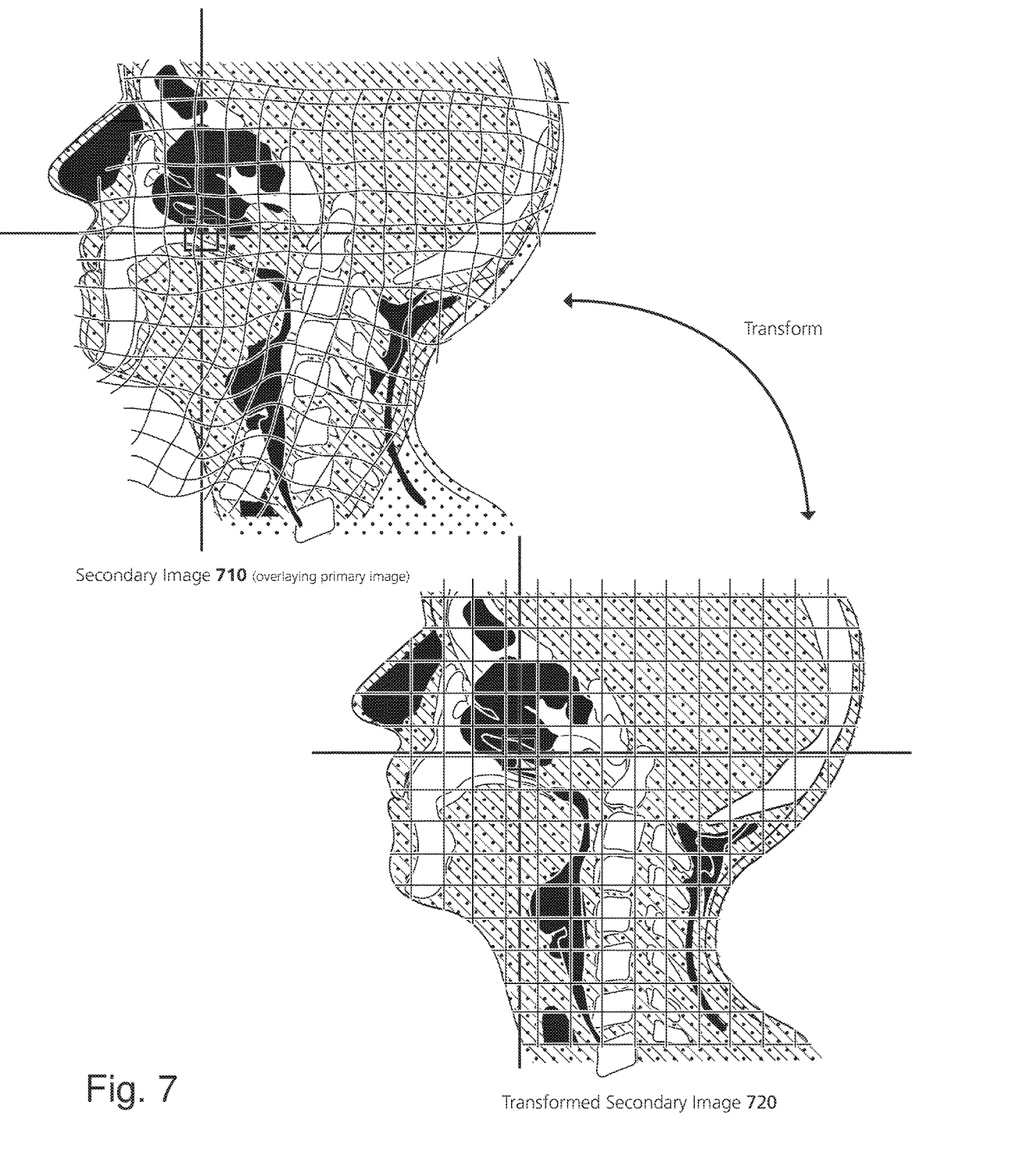
FIG. 7 illustrates an exemplary visualization depicting a transformation of an image according to various aspects.

FIG. 7 illustrates an exemplary visualization depicting a transformation of an image according to various aspects. As shown in FIG. 7, secondary image 710 is displayed overlaying a primary image. The visual aid or grid, as in FIG. 6, is also illustrated. In FIG. 7, to differentiate the two images for the purposes of this disclosure, the secondary image 710 is shaded with a parallel hatching effect and the primary image is shaded with stipple effect. It is to be appreciated that such shading is shown to promote comprehension and is not intended to be a feature of the visualization or visual aid as claimed.

By overlaying the secondary image and the primary image, any misalignment is readily apparent. After application of the registration transform, a transformed secondary image 720 is displayed. By maintaining an overlay of the secondary image on the primary image, alignment of features (e.g. anatomy), and thus accuracy of the registration, is readily perceived. Further, the visual aid enables evaluation and understanding of movement of features as a result of the transform.

Figure 8:
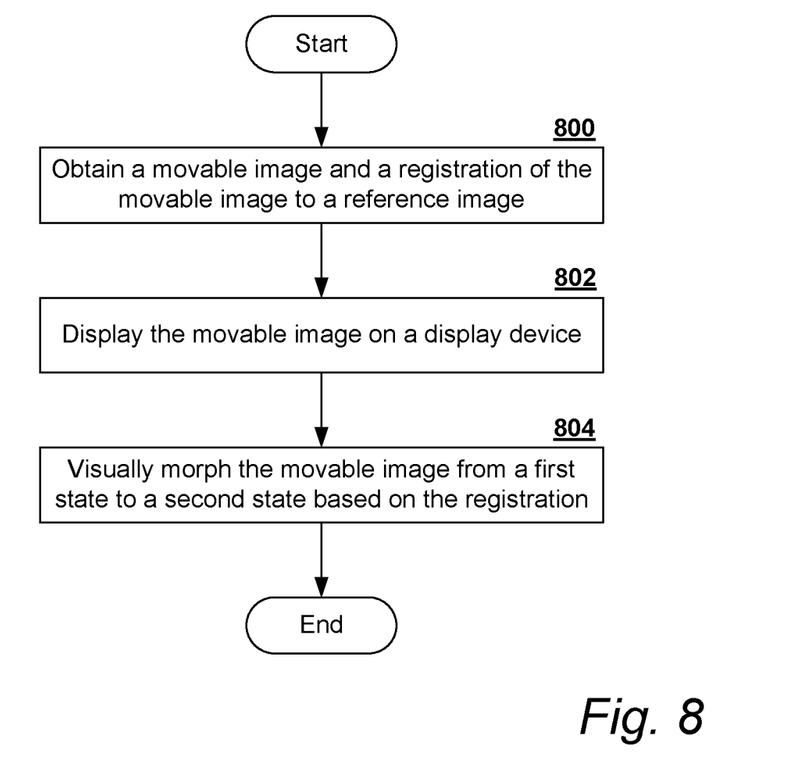
FIG. 8 is a flow diagram of an exemplary, non-limiting method for visualizing a registration between at least two images.

FIG. 8 illustrates a flow diagram of an exemplary, non-limiting method for visualizing a registration between at least two images. The method of FIG. 8 can be performed, for example, by registration visualization system 100, 200 and/or visualization application 310 executed on computing device 300 as described above. At 800, a movable image and a registration of the movable image to a reference image are obtained. The registration can be obtained computationally according to a registration technique (e.g., rigid or non-rigid). In another example, the registration is obtained from a data store (remote or local). Similarly, the movable image and the reference image can be stored on an image storage server (e.g., PACS server), retrieved from a data store, and/or received from an imaging apparatus. At 802, the movable image is displayed on a display device. At 804, the movable image is visually morphed from a first state to a second state based on the registration. For example, the first state can correspond to the movable image having a baseline transformation (e.g. no transformation or a rigid transformation) applied and the second state can correspond to the movable image fully transformed according to the registration. Accordingly, visually morphing can include animating the movable image through various intermediate states between the first state and the second state.

As utilized herein, "no transformation" may refer to a state of the movable image in which no final registration is applied. For instance, a reference transform or registration (such as a best-fit rigid registration) can be previously applied to the movable image. Accordingly, the first state may correspond to the movable image having no transformation applied based on the final registration, but having transformation applied according to the reference registration. In other examples without the reference transform or registration included, the first state may correspond to an original, unaltered state of the movable image.

Figure 9:
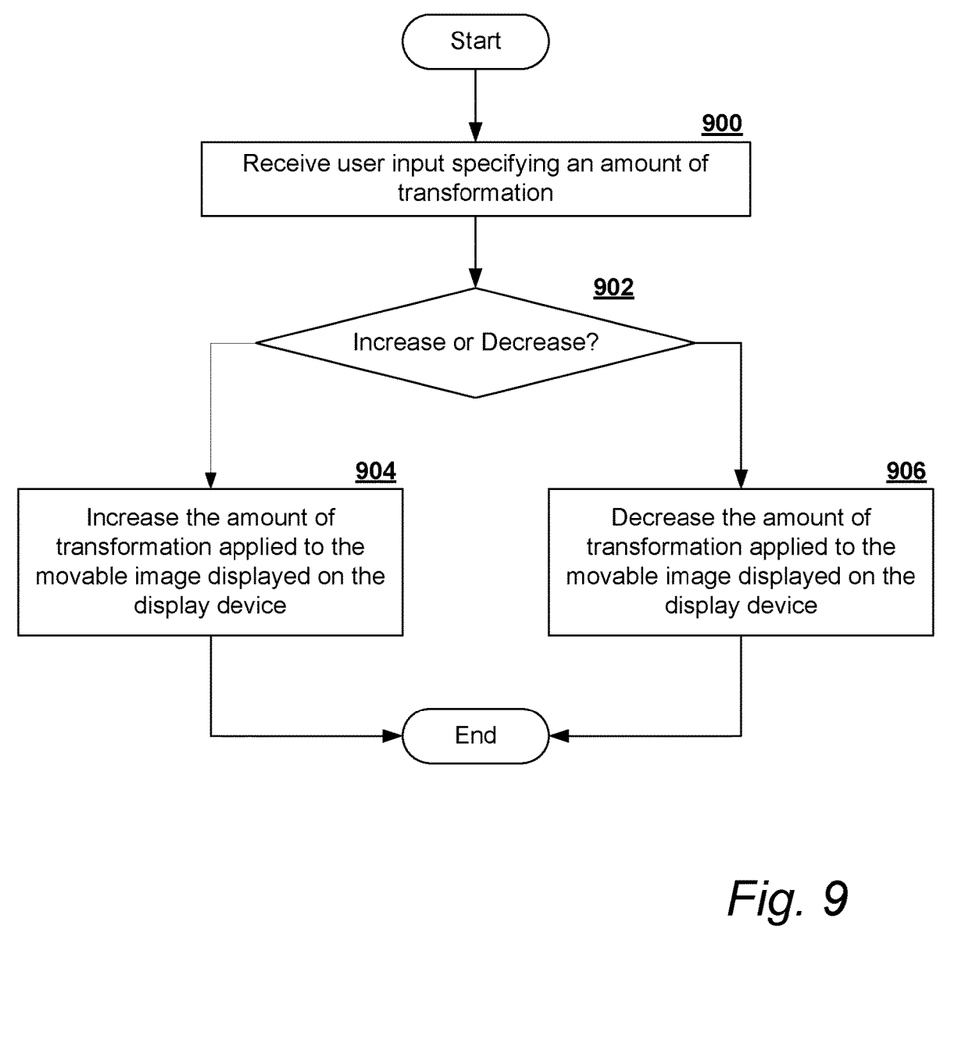
FIG. 9 is a flow diagram of an exemplary, non-limiting method for generating a visualization of a registration transform responsive to user input.

Referring now to FIG. 9, a flow diagram of an exemplary, non-limiting method for generating a visualization of a registration transform responsive to user input is illustrated. The method of FIG. 9 can be performed, for example, by registration visualization system 100, 200 and/or visualization application 310 executed on computing device 300 as described above. At 900, user input is received. The user input can specify an amount of transformation to be applied to the movable image in accordance with the registration transform. The amount of transformation can be specified as an absolute amount or a relative amount with respect to current state of the movable image. At 902, a determination is made as to whether the amount of transformation specified in the user input indicates an increase or a decrease. When an increase is specified, the amount of transformation applied to movable image displayed is increased at 904. In one example, when the user input indicates an absolute value, the amount of transformation applied matches that absolute value. When a relative value is indicated, the amount of transformation is increased by a degree corresponding to the relative value. When a decrease is specified, the amount of transformation applied to the movable image is decreased to an absolute value or by a relative value, whichever is indicated in the user input.

Figure 10:
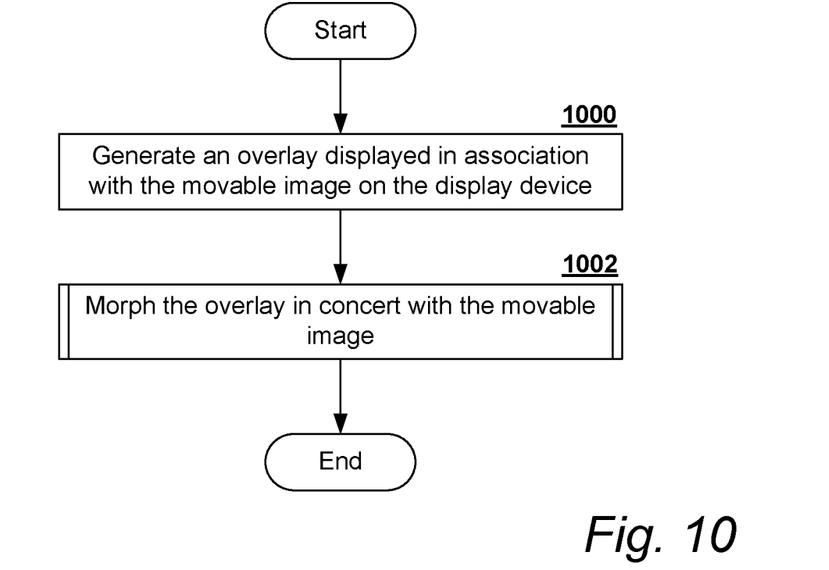
FIG. 10 is a flow diagram of an exemplary, non-limiting method for utilizing an overlay as a visualization aide for a registration.
Figure 11:
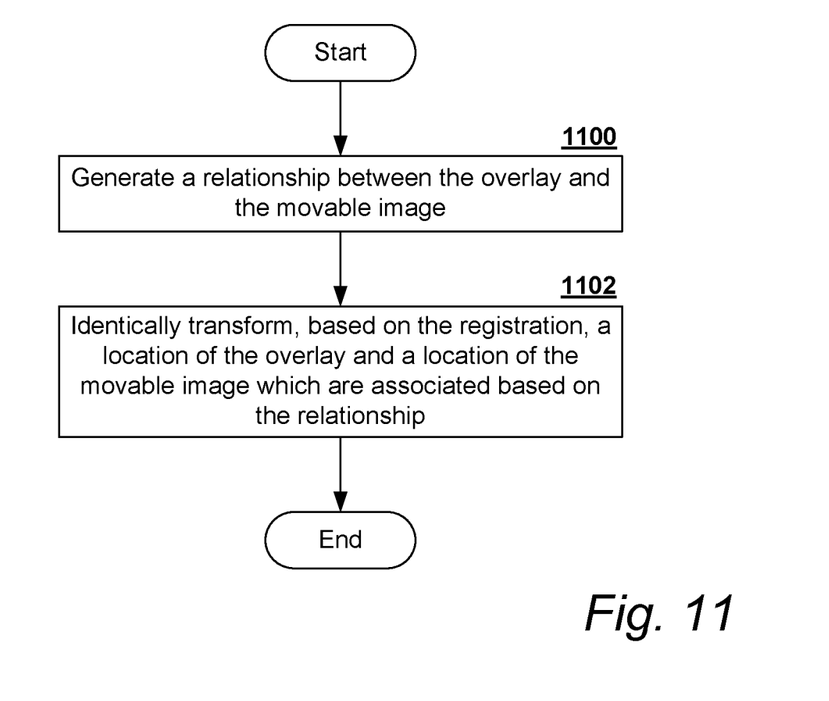
FIG. 11 is a flow diagram of an exemplary, non-limiting method for transforming the overlay based on an image registration.

Referring to FIG. 10, a flow diagram of an exemplary, non-limiting method for utilizing an overlay as a visualization aid for a registration is depicted. At 1000, a visual aid is generated. The visual aid is displayed in association with a movable image on a display device. At 1002, the visual aid is morphed, according to a registration, in concert with the movable image. For instance, turning to FIG. 11, an exemplary, non-limiting method for transforming the visual aid based on an image registration is illustrated. At 1100, a relationship is generated between the visual aid and the movable image. For example, by overlaying the visual aid on the movable image, points of the visual aid are made to correspond to or lay on top of respective points of the movable image. Thus, a relationship is created. At 1102, a location on the visual aid and a location on the movable image, associated based on the relationship, are identically transformed based on the registration.

Exemplary Computing Device

As mentioned, advantageously, the techniques described herein can be applied to any device where it is desirable to provide a visualization of a registration of an image. It can be understood, therefore, that handheld, portable and other computing devices and computing objects of all kinds are contemplated for use in connection with the various embodiments of a registration visualization system. Accordingly, the below general purpose computer described below in FIG. 12 is but one example of a computing device.

Embodiments can partly be implemented via an operating system, for use by a developer of services for a device or object, and/or included within application software that operates to perform one or more functional aspects of the various embodiments described herein. Software may be described in the general context of computer-executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is considered limiting.

Figure 12:
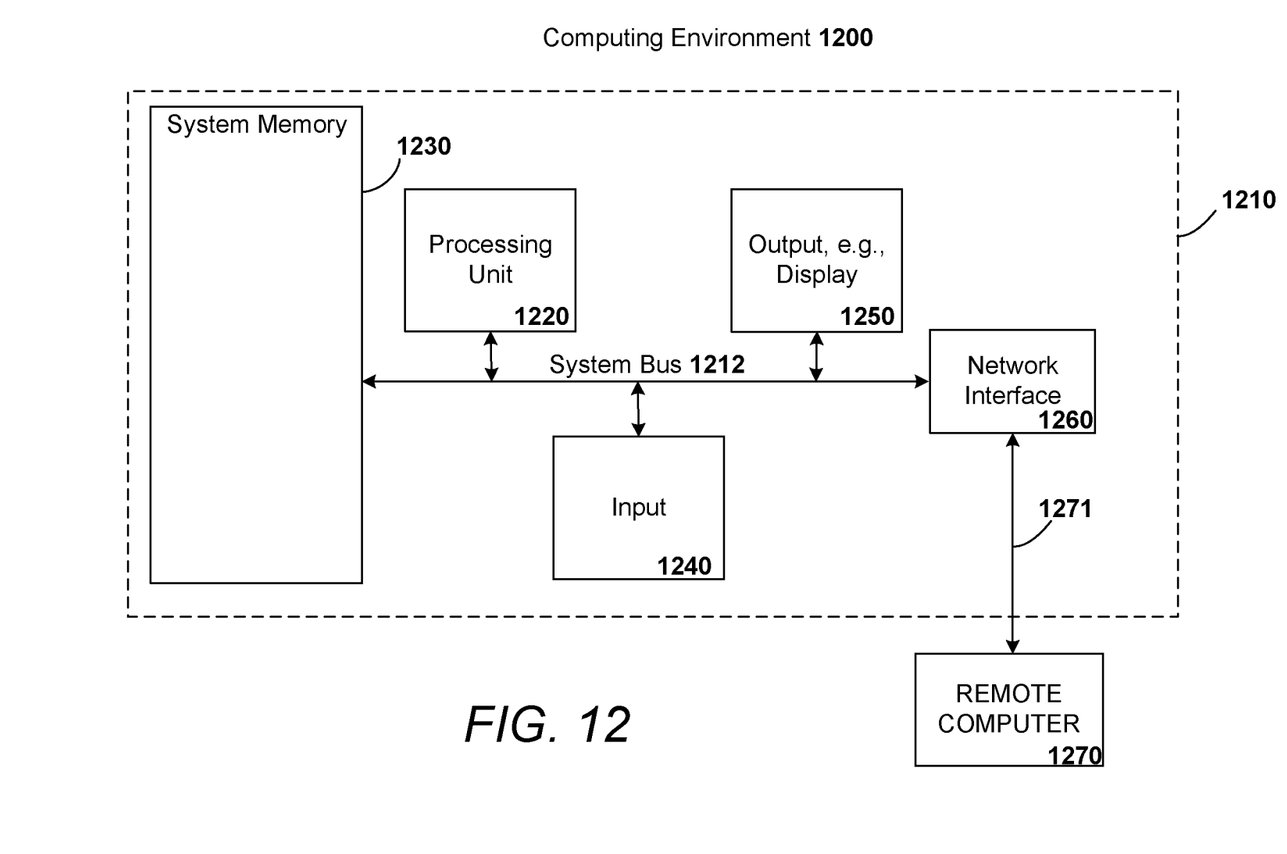
FIG. 12 is a block diagram representing an exemplary, non-limiting computing system or operating environment in which one or more aspects of various embodiments described herein can be implemented.

FIG. 12 thus illustrates an example of a suitable computing system environment 1200 in which one or aspects of the embodiments described herein can be implemented, although as made clear above, the computing system environment 1200 is only one example of a suitable computing environment and is not intended to suggest any limitation as to scope of use or functionality. In addition, the computing system environment 1200 is not intended to be interpreted as having any dependency relating to any one or combination of components illustrated in the exemplary computing system environment 1200.

With reference to FIG. 12, an exemplary device for implementing one or more embodiments includes a general purpose computing device in the form of a computer 1210. Components of computer 1210 may include, but are not limited to, a processing unit 1220, a system memory 1230, and a system bus 1222 that couples various system components including the system memory to the processing unit 1220.

Computer 1210 typically includes a variety of computer readable media and can be any available media that can be accessed by computer 1210. The system memory 1230 may include computer storage media in the form of volatile and/or nonvolatile memory such as read only memory (ROM) and/or random access memory (RAM). By way of example, and not limitation, system memory 1230 may also include an operating system, application programs, other program modules, and program data. According to a further example, computer 1210 can also include a variety of other media (not shown), which can include, without limitation, RAM, ROM, EEPROM, flash memory or other memory technology, compact disk (CD) ROM, digital versatile disk (DVD) or other optical disk storage, or other tangible and/or non-transitory media which can be used to store desired information.

A user can enter commands and information into the computer 1210 through input devices 1240. A monitor or other type of display device is also connected to the system bus 1222 via an interface, such as output interface 1250. In addition to a monitor, computers can also include other peripheral output devices such as speakers and a printer, which may be connected through output interface 1250.

The computer 1210 may operate in a networked or distributed environment using logical connections to one or more other remote computers, such as remote computer 1270. The remote computer 1270 may be a personal computer, a server, a router, a network PC, a peer device or other common network node, or any other remote media consumption or transmission device, and may include any or all of the elements described above relative to the computer 1210. The logical connections depicted in FIG. 12 include a network 1272, such local area network (LAN) or a wide area network (WAN), but may also include other networks/buses. Such networking environments are commonplace in homes, offices, enterprise-wide computer networks, intranets and the Internet.

As mentioned above, while exemplary embodiments have been described in connection with various computing devices and network architectures, the underlying concepts may be applied to any network system and any computing device or system in which it is desirable to implement a subscription-based diagnostic software service.

Also, there are multiple ways to implement the same or similar functionality, e.g., an appropriate API, tool kit, driver code, operating system, control, standalone or downloadable software objects, etc. which enables applications and services to take advantage of the techniques provided herein. Thus, embodiments herein are contemplated from the standpoint of an API (or other software object), as well as from a software or hardware object that implements one or more embodiments as described herein. Thus, various embodiments described herein can have aspects that are wholly in hardware, partly in hardware and partly in software, as well as in software.

As utilized herein, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the term "exemplary" is intended to mean "serving as an illustration or example of something."

Illustrative embodiments have been described, hereinabove. It will be apparent to those skilled in the art that the above devices and methods may incorporate changes and modifications without departing from the general scope of the claimed subject matter. It is intended to include all such modifications and alterations within the scope of the claimed subject matter. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method, comprising: receiving a first image;
   receiving a registration of the first image to a second image; outputting the first image to a display device;
   generating an overlay displayed in association with the first image on the display device; visually morphing the first image, as displayed on the display device, from a first state to a second state based at least in part on the registration; and
   morphing the overlay in concert with the first image such that a location of the overlay morphs identically, based in part on the registration, to a location of the first image on which the location overlays.

2. The method of claim 1, further comprising receiving a user input via an input device.

3. The method of claim 2, wherein the user input effects a change in an amount of transformation, based on the registration, to apply to the first image.

4. The method of claim 3, wherein the amount of transformation selectable inclusively ranges between a first level corresponding to no transformation applied to a second level corresponding to a complete transformation applied.

5. The method of claim 3, wherein the user input specifies an increase in the amount of transformation, and
   wherein morphing the first image comprises increasing the amount of transformation applied for the first state to generate the second state.

6. The method of claim 3, wherein the user input specifies a decrease in the amount of transformation, and
   wherein morphing the first image comprises decreasing the amount of transformation applied for the first state to generate the second state.

7. The method of claim 1, wherein morphing comprises visually displaying, on the display device, a transition of the first image from the first state to the second state.

8. The method of claim 7, wherein the transition is an animation.

9. The method of claim 1, wherein the first state corresponds to an original state of the first image and the second state corresponds to a fully registered state of the first image according to the registration.

10. The method of claim 1, wherein the overlay comprises a grid graphically overlaying the first image.

11. The method of claim 1, wherein morphing the overlay in concert with the first image comprises:
    maintaining a relationship between the overlay and the first image; and spatially transforming a location of the overlay and a location of the first image, associated by the relationship, identically in accordance with the registration.

12. The method of claim 1, further comprising configuring the overlay such that a feature of the overlay is mapped to a point of interest of the first image.

13. A system, comprising: a transformation engine configured to apply a spatial transformation to a first image to transition the first image from a first state to a second state, wherein a registration of the first image to a second image specifies the spatial transformation;
a display engine configured to output a visualization of the spatial transformation applied to the first image to a display device, wherein the visualization demonstrates movement of the first image from the first state to the second state based on the spatial transformation applied and the visualization includes a visual aid overlaying the first image, the transformation engine being further configured to apply the spatial transformation to the visual aid such that a location of the visual aid is transformed identically to an image location on which the location of the visual aid overlays;
a computer-readable storage medium having stored thereon computer-executable instructions for the transformation engine and the display engine such that the computer-executable instructions, when executed by a processor, configure the processor to implement the transformation engine and the display engine.

14. The system of claim 13, further comprising a registration engine configured to generate the registration of the first image to the second image.

15. The system of claim 14, wherein the registration engine utilizes a deformable registration technique to generate the registration.

16. The system of claim 13, wherein the visual aid includes a feature mapped to a point of interest of the first image.

17. The system of claim 13, wherein the visual aid is a grid.

18. The system of claim 13, wherein the transformation engine is further configured to determine an amount of transformation to apply to the first image, based on the registration, to generate the second state of the first image.

19. The system of claim 18, wherein the amount of transformation indicates a relative change from a first level of transformation applied for the first state to a second level of transformation corresponding to the second state.

20. The system of claim 19, wherein the relative change represents one of an increase or a decrease in a level of transformation between the first state and the second state.

21. The system of claim 13, wherein the first state and the second state represent respective states of spatial transformation on a spectrum from an original, untransformed state to a fully transformed state in accordance with the registration.

22. The system of claim 13, further comprising a user interface configured to generate a graphical user interface displayable by the display engine and to obtain a user input, via an input device, with respect to the graphical user interface.

23. The system of claim 22, wherein the transformation engine determines at least one of the first state or the second state based at least in part on the user input.

24. The system of claim 22, wherein, responsive to the user input, the transformation engine applies the spatial transformation to the first image and the display engine interactively displays the movement of the first image from the first state to the second state.

25. The system of claim 13, wherein the transformation engine is further configured to identify a level of transformation to apply and to scale a full transformation specified by the registration according to the level of transformation.

26. A computer-readable storage medium having stored thereon computer-executable instructions that, when executed by a processor, configure the processor to: apply a spatial transformation to a first image to transform the first image from a first state to a second state;
generate a visualization of movement of one or more portions of the first image due to application of the spatial transformation, wherein the visualization is generated as a grid overlaying the first image;
output the visualization to a display device to demonstrate the movement of the one or more portions for a user; and
apply the spatial transformation to the grid, wherein a grid location is transformed identically to an image location on which the grid location overlays.

27. The computer-readable storage medium of claim 26, wherein the computer-executable instructions stored thereon further configure the processor to output the visualization as an animation.

28. The computer-readable storage medium of claim 26, wherein the computer-executable instructions stored thereon further configure the processor to configure the grid such a feature of the grid is mapped to a point of interest of the first image.

29. The computer-readable storage medium of claim 26 wherein the computer-executable instructions stored thereon further configure the processor to receive a user input, and to interactively control the output of the visualization responsive to the user input.

30. A method, comprising:
receiving a first image;
receiving a registration of the first image to a second image;
outputting the first image to a display device;
receiving a user input via an input device, wherein the user input effects a change in an amount of transformation, based on the registration, to apply to the first image; and
visually morphing the first image, as displayed on the display device, from a first state to a second state based at least in part on the registration.

31. The method of claim 30, wherein the amount of transformation selectable inclusively ranges between a first level corresponding to no transformation applied to a second level corresponding to a complete transformation applied.

32. The method of claim 30, wherein the user input specifies an increase in the amount of transformation, and
wherein morphing the first image comprises increasing the amount of transformation applied for the first state to generate the second state.

33. The method of claim 30, wherein the user input specifies a decrease in the amount of transformation, and
wherein morphing the first image comprises decreasing the amount of transformation applied for the first state to generate the second state.

34. The method of claim 30, wherein morphing comprises visually displaying, on the display device, a transition of the first image from the first state to the second state.

35. The method of claim 34, wherein the transition is an animation.

36. The method of claim 30, wherein the first state corresponds to an original state of the first image and the second state corresponds to a fully registered state of the first image according to the registration.

37. The method of claim 30, further comprising:
generating an overlay displayed in association with the first image on the display device; and
morphing the overlay in concert with the first image.

38. The method of claim 37, wherein the overlay comprises a grid graphically overlaying the first image.

39. The method of claim 37, wherein morphing the overlay in concert with the first image comprises:
maintaining a relationship between the overlay and the first image; and
spatially transforming a location of the overlay and a location of the first image, associated by the relationship, identically in accordance with the registration.

40. The method of claim 37, further comprising configuring the overlay such that a feature of the overlay is mapped to a point of interest of the first image.

* * * * *